United States Patent [19]

Gallopo et al.

[11] Patent Number: 4,915,948
[45] Date of Patent: Apr. 10, 1990

[54] TABLETS HAVING IMPROVED BIOADHESION TO MUCOUS MEMBRANES

[75] Inventors: Andrew R. Gallopo, Garfield; Steven S. Dills, Wharton, both of N.J.

[73] Assignee: Warner-Lambert Company, Morris Plains, N.J.

[21] Appl. No.: 91,575

[22] Filed: Aug. 31, 1987

[51] Int. Cl.[4] ............................................. A61F 13/00
[52] U.S. Cl. .................... 424/435; 424/464; 424/499
[58] Field of Search ..................... 424/435, 464, 499

[56] References Cited

U.S. PATENT DOCUMENTS

| | | | |
|---|---|---|---|
| 3,911,099 | 10/1975 | DeFoney et al. | 424/435 |
| 3,996,934 | 12/1976 | Zaffaroni | 128/268 |
| 4,226,848 | 10/1980 | Nagai et al. | 424/14 |
| 4,250,163 | 9/1981 | Nagai et al. | 424/22 |
| 4,286,592 | 9/1981 | Chandrasekaran | 128/260 |
| 4,292,299 | 9/1981 | Suzuki | 424/16 |
| 4,572,832 | 2/1986 | Kigasawa | 424/435 |
| 4,597,959 | 7/1986 | Barr | 424/19 |
| 4,615,697 | 10/1986 | Robinson | 604/890 |

FOREIGN PATENT DOCUMENTS

| | | | |
|---|---|---|---|
| 0762574 | 8/1971 | Belgium | 424/435 |
| 2712161 | 9/1978 | Fed. Rep. of Germany | 424/435 |
| 3534981 | 4/1986 | Fed. Rep. of Germany | 424/435 |
| 61-122211 | 6/1986 | Japan | 424/435 |
| 1240411 | 7/1971 | United Kingdom . | |
| 2156215 | 10/1985 | United Kingdom . | |
| 2161073 | 1/1986 | United Kingdom . | |

Primary Examiner—Thurman K. Page
Attorney, Agent, or Firm—Henry C. Jeannette

[57] ABSTRACT

A tablet having improved bioadhesion to mucous membranes is disclosed. The tablet comprises effective amounts of a water-soluble biopolymer selected from the group consisting of a xanthan gum, a pectin and mixtures thereof; and a solid polyol having a solubility at room temperature in water greater than about 20 grams of polyol per 100 g of solution. Preferably the biopolymer is xanthan gum and the polyol is a sugar alcohol selected from the group consisting of sorbitol, xylitol, and mixtures thereof.

24 Claims, 3 Drawing Sheets

TABLETS HAVING IMPROVED BIOADHESION TO MUCOUS MEMBRANES

FIELD

This invention relates to compositions containing a bioadhesive material and a polyol of a certain threshold solubility. The combination of the bioadhesive material and the polyol results in a composition having a bioadhesion greater than that of the bioadhesive alone.

BACKGROUND

Interest within the industry in providing various vehicles for the slow delivery of active ingredients to the body has resulted in a variety of bioadhesive delivery forms. Various types of materials found to adhere to mucous membranes without exerting a harmful effect have been formed into tablets designed to provide a delivery system for the administration of drugs over a period of time. Ideally the drug, or other active agent, is incorporated into a bioadhesive tablet and the tablet is placed in contact with a mucous membrane to which it adheres. The drug, or other active agent, is dissolved from the tablet and delivered into a body cavity or into the body through the mucous membrane. A problem associated with such a delivery system is related to the tenacity with which the tablet adheres to the mucous membrane. Sometimes the tablet becomes separated from the mucous membrane before the desired dose of active material has been completely delivered.

U.S. Pat. No. 3,996,934 issued to Zaffaroni on December 14, 1976 discloses a bandage for continuously administering controlled quantities of systemically active drugs through the skin or mucosa. The bandage comprises a laminate of (1) a backing member defining one surface of the bandage, and, defining the other face surface of the bandage, (2) at least one reservoir comprised of a systemically active drug formulation confined within a wall member, and (3) means to secure the bandage. The wall member is formed from drug release rate controlling material to continuously meter the flow of a therapeutically effective amount of drug from the reservoir to the skin or mucosa at a controlled and predetermined rate over a prolonged period of time.

U.S. Pat. No. 4,226,848 and U.S. Pat. No. 4,250,163 issued to Nagai et al on Oct. 7, 1980, and Feb. 10, 1981, respectively, are directed to a method for administering a medicament which comprises adhering to the mucosa of the oral or nasal cavity a pharmaceutical preparation comprising (a) a water-swellable and mucosa-adhesive polymeric matrix, and (b) a pharmaceutically effective amount of the medicament dispersed therein. The polymeric matrix comprises about 50–95% by weight of a cellulose ether and about 50 to 5% by weight of a homo or copolymer of acrylic acid or a pharmaceutically acceptable salt thereof. According to this patent, the pharmaceutical preparation may further contain at least one known excipient such as a lubricant, binder, vehicle, coloring agent, taste controlling agent and color controlling agent as required for improving the appearance, odor or taste of the pharmaceutical preparation. The lubricants include talc, stearic acid, stearate salts, and waxes. Examples of the binders include starch, dextrin, tragacanth, gelatin, polyvinyl pyrrolidone and polyvinyl alcohol. The vehicles include starch, crystalline cellulose, dextrin, mannitol, sorbitol, and anhydrous calcium phosphates. The agents for controlling tastes and smells are citric acid, fumaric acid, tartaric acid, menthol, and citrus perfumes.

U.S. Pat. No. 4,286,592 issued to Chandrasekaran on Sept. 1, 1981 is directed to a bandage for administering drugs to the skin. The bandage is a laminate of a backing layer, a drug reservoir layer, and a contact adhesive layer. The bandage consists essentially of a sandwich type laminate of: (a) a backing lamina that is substantially impermeable to the drug, one face of which forms the top of the bandage; (b) a drug reservoir lamina adjacent the opposite face of the backing layer comprising the drug dispersed in a carrier that is permeable to the drug; and (c) a contact adhesive lamina adjacent and below the drug reservoir lamina comprising a contact adhesive composition that is permeable to the drug.

U.S. Pat. No. 4,292,299 issued to Suzuki et al on Sept. 29, 1981 is directed to a slow-releasing medical preparation to be administered by adhering to the wet mucous surface comprising an adhesive layer and a nonadhesive layer. The adhesive layer is composed of a polymer which has the adhesiveness to the wet mucous surface and a property to swell upon moistening. The nonadhesive layer is either water soluble or disintegrable which has no adhesiveness to the wet mucous surface. At least one of the layers has a medicament. Polymers disclosed as useful for the adhesive layer include homopolymers of acrylic acid; copolymers of acrylic acid; hydrophilic vinyl polymers; hydrophilic cellulose derivatives; polysaccharides such as hydroxypropyl starch, alginic acid, sodium alginate, and tragacanth gum or their derivatives; and such derivatives having improved swellability as collagen, gelatine or radiobridged gelatine, and chemically modified gelatine. The adhesive layer may further contain other ingredients such as a binder, disintegrator, coloring agent, corrigent, and lubricant provided that the layer maintains said adhesiveness to the wet mucous surface. Examples of ingredients which may comprise the nonadhesive layer include lactose, glucose, sucrose, starch, crystalline cellulose, dextrin, cyclodextrin, silicic acid anhydride, aluminum silicate, talc, calcium stearate, magnesium stearate, beeswax, polyethylene glycol, and polyphosphate. The lubricants which may be mentioned and which are used as occasion demands are talc, stearic acid, stearate salts, and waxes. The binders include, for instance, starch, dextrin, tragacanth, gelatine, polyvinylpyrrolidone, polyvinyl alcohol, hydroxypropyl cellulose, crystalline cellulose, hydroxypropyl methyl cellulose, ethyl cellulose, carboxymethyl cellulose, etc. The disintegrators include starch, crystalline cellulose, calcium carboxymethyl cellulose, etc. The excipients include starch, crystalline cellulose, dextrin, lactose, mannitol, sorbitol, calcium phosphoric acid anhydride, etc. The corrigents include citric acid, fumaric acid, tartaric acid, menthol, citrus perfumes, etc.

U.S. Pat. No. 4,572,832 issued to Kigasawa et al on Feb. 25, 1986 is directed to a soft buccal containing a pharmaceutically effective amount of a medicament to be absorbed through the oral mucosa, a water-soluble protein, a polyhydric alcohol, and a fatty acid ester and/or a carboxyvinyl polymer. The water-soluble protein includes natural proteins of animal or plant origin and non-natural ones which are artificially produced peptides. The polyhydric alcohol includes glycols, triols and polyols. The polyhydric alcohols include cellulose and sugars. Typical of the sugars are monosaccharides, disaccharides and polysaccharides. The monosaccharides include glucose, galactose, fructose, mannose, mannitol, and sorbitol. The disaccharides may be the dimers of such monosaccharides as maltose, lactose and sucrose. The polysaccharides include the genuine polysaccharides which are condensates of at least 7 units of the above-mentioned monosaccharides such as starch and its derivatives, dextrin, dextran, chitin, alginic acid, glycogen, etc., and the composite condensates of at least 7 units of one of the abovementioned monosaccharides with one of non-sugar substances such as mannan, pectin, gum arabic, etc. Other additives which may be used include, flavors (saccharin sodium, glycyrrhizin, malt syrup, citric acid, tartaric acid, menthol, lemon oil, citrus flavor, common salt, etc.); stabilizers/preservatives; colors; excipients/-disintegration adjusting agents; water-soluble polymers other than water-soluble proteins; and stearic acid and its salts, talc, palmitic acid, and other substances known as emulsifiers, dispersants, binders, thickeners, etc.

U.S. Pat. No. 4,597,959 issued to Barr on July 1, 1986 discloses a breath freshener composition, in a wafer form having slow release. The composition comprises a multiplicity of microencapsulated liquid droplets of flavoring materials. The microencapsulated droplets are soluble in saliva to slowly release the flavoring materials. The microencapsulates are present in a wafer form which comprises a base of gelatin, gum arabic and/or Carrageenen with an adhesive distributed throughout. In this way the wafer can be directly applied to the gums and palate or the wafer can be directly applied to the inner or outer surfaces of full or partial dentures.

U.S. Pat. No. 4,615,697 issued to Robinson on Oct. 7, 1986 discloses controlled release compositions and methods utilizing those compositions. The compositions include a bioadhesive and an effective amount of a treating agent. The bioadhesive comprises a water-swellable, but water-insoluble, fibrous, cross-linked carboxy-functional polymer. In typical practice, the ratio by weight of the bioadhesive to the treating agent in the composition is about 200,000:1 to about 1:100.

British Patent Specification No. 1,240,411 whose complete specification was published July 21, 1971 discloses a tab for application to the mucous membrane which tab is capable of adhering thereto by moisture. The tab is saturated with or coated with at least one anaesthetic agent, disinfectant agent and dye for marking the membrane. Generally, the tab is formed from paper, textile material, plastics material or a mixture thereof. Coating may be with the aid of an adhesive such as albumin, tragacanth or a cellulose adhesive.

U.K. Patent Application No. GB 2156215A published on Oct. 9, 1985 discloses a percutaneous absorption type preparation which comprises a backing and an adhesive layer. The backing is readily conformable to skin or mucosa and is substantially impermeable to a drug absorbed through the skin or mucosa. The adhesive layer comprises a polymer which is pressure-adhesive at room temperature, and a drug present in the polymer. The drug is present in the adhesive layer in an amount greater than its saturated solubility in the polymer and the excess amount of the drug greater than the saturated solubility is dispersed in the polymer in the form of re-crystallized fine particles having a substantially uniform size.

U.K. Patent Application No. GB 2161073A published Jan. 8, 1986 discloses a transdermal therapeutic system adapted for the delivery of biologically active agents for an extended time period comprising, in combination, a matrix containing the agent uniformly distributed therein with the intended body distal surface of said matrix having a fibrous reinforcing means imbedded therein. The matrix being capable of adherence to the skin with a peel strength sufficient to maintain the system in place for the extended time and being sufficiently low to be removed without discomfort.

Thus, buccal tablets possessing the ability to adhere to the oral mucosa and release active agents (drug or cosmetic) to the oral cavity are known in the art. The tablets are composed of a variety of natural or synthetic polymeric materials. In formulating the compositions for such tablets attention is focused on providing tablets which are adherent during the period of use, i.e., stay in place, are capable of continued release of an active ingredient over a desired time period, and are comfortable to the user. Thus, a novel composition which provides improved adhesion and is capable of continual release of an active ingredient would be a welcome contribution to the art. This invention provides such a composition.

SUMMARY OF THE INVENTION

This invention provides compositions having improved bioadhesion to mucous membranes comprising a bioadhesive material and an adhesion enhancing material. The use of an adhesion enhancing material results in significantly better adhesion of the composition to mucous membranes in comparison to compositions which do not have the enhancing material.

Generally, the bioadhesive material comprises a water-soluble natural biopolymer selected from the group consisting of a xanthan gum, a pectin, and mixtures thereof. The adhesion enhancing material is generally a polyol, and particularly a sugar alcohol, having a solubility in water at rm temperature (about 25° C.) which is greater than about 20 g/100 g (g polyol/100 g of solution). The amount of adhesion enhancing material is suitably selected to provide an increase in bioadhesion of at least about 10% as measured by the force necessary to separate the composition from a mucous membrane.

DETAILED DESCRIPTION OF THE INVENTION

Figure 1:
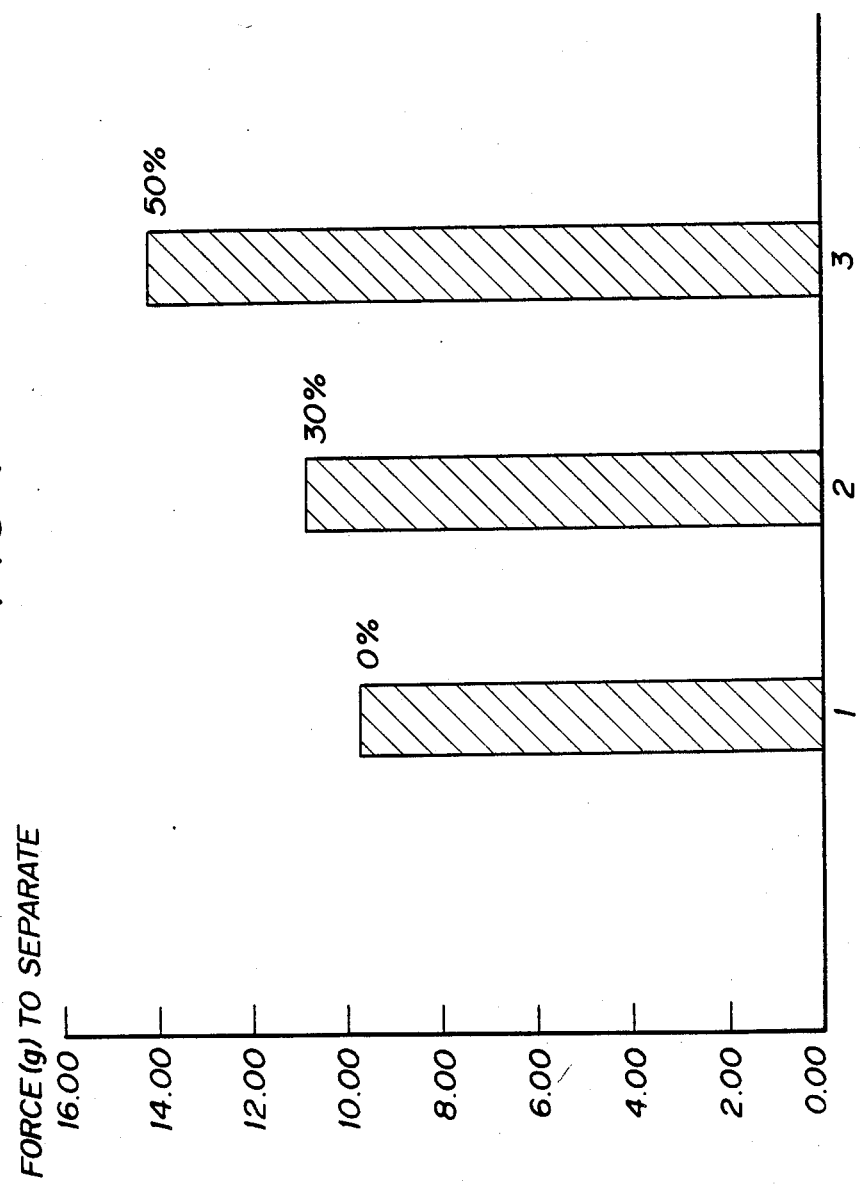
FIG. 1 is a bar graph illustrating the increase in bioadhesion of xanthan gum tablets containing 30% by wt. and 50% by wt. sorbitol in comparison to xanthan gum tablets containing 0% by wt. sorbitol.

This invention provides a tablet having improved bioadhesion to mucous membranes comprising:

(a) an effective amount of a water-soluble natural biopolymer selected from the group consisting of a xanthan gum, a pectin and mixtures thereof; and (b) an effective amount of a solid polyol having a solubility at room temperature in water greater than about 20 grams of polyol per 100 g of solution (20 g/100 g).

The tablets of this invention are useful for delivering active agents to the mouth over a period of time (i.e., sustained release) while adhering to the mucous membranes of the mouth. As used herein, "mucous membranes" is meant to include all the moist tissue structures in the mouth to which a tablet can adhere to, including the buccal and lingual tissue, the upper palate, and the like.

The bioadhesive material utilized comprises a water-soluble natural biopolymer selected from the group consisting of a xanthan gum, a pectin and mixtures thereof. Since xanthan gum and pectin are water-soluble biopolymers, it is contemplated that similar biopolymers may also prove useful.

Xanthan gum is a high-molecular-weight natural carbohydrate, or, more specifically, polysaccharide. Xanthan gum defines the exocellular biopolysaccharide which is produced in a pure culture fermentation process by the microorganism *Xanthomonas campestris*.

In the fermentation, *Xanthomonas campestris* is cultured in a well-aerated medium containing commercial glucose, a suitable nitrogen source, dipotassium hydrogen phosphate, and appropriate trace elements. To provide seed for the final fermentation, *Xanthomonas campestris* is grown in several stages with associated identification tests prior to introduction into the final fermentation medium.

At the conclusion of the fermentation process, xanthan gum is recovered by precipitation in isopropyl alcohol, then dried and milled.

The molecular weight of the polymer (i.e., xanthan gum) is probably in the order of 2 million but has been reported to be as high as 13–50 million. These differences are probably due to association phenomena between polymer chains.

Three different monosaccharides are found in xanthan gum: mannose, glucose, and glucuronic acid (as a mixed potassium, sodium, and calcium salt).

Each repeating block contains five sugar units consisting of two glucose units, two mannose units, and one glucuronic acid unit. The main chain of xanthan gum is built up of $\beta$-D-glucose units linked through the 1-and 4-positions; i.e. the chemical structure of the main chain of xanthan gum is identical to the chemical structure of cellulose. The side chain consists of the two mannose units and the glucuronic acid unit. The terminal $\beta$-D-mannose unit is linked glycosidically to the 4-position of $\beta$-D-glucuronic acid, which in turn is linked glycosidically to the 2-position of $\alpha$-D-mannose. This three-sugar side chain is linked to the 3-position of every other glucose residue in the main chain. The distribution of the side chains is unknown. Also, about half of the terminal D-mannose residues carry a pyruvic acid residue ketalically linked to the 4- and 6-positions. The distribution of these pyruvate groups is unknown. The non-terminal D-mannose unit in the side chain contains an acetyl group at position 6.

Additional information concerning xanthan gum may be found in *Xanthan Gum*. second edition, a technical bulletin of Kelco, Division of Merck & Co., Inc., the disclosure of which is incorporated herein by reference thereto.

Pectin is a naturally occurring hydrocolloid whose structure is mainly that of a partially methylated polygalacturonic acid. According to *The Merck Index*, tenth edition, pectin has a molecular weight of 20,000–400,000. Additional information may be found in Windholz, Martha (Editor), *The Merck Index*, tenth edition, published by Merck & Co., Inc., Rahway, N.J., copyright 1983, page 1013, the disclosure of which is incorporated herein by reference thereto.

A sufficient amount of the natural biopolymer, preferably a xanthan gum, is used to provide a base for the incorporation of the other ingredients and active agents described below which are used and to provide adhesion to a mucous membrane. Generally, about 40 to about 80% by weight, based on the total weight of the tablet, is suitable, with about 45 to about 75% by weight being preferred, and about 50 to about 70% by weight being most preferred. More preferred tablets contain the natural biopolymer in amounts of about 50% by weight of the tablet.

The natural biopolymer, preferably a xanthan gum, is combined with an adhesion enhancing material such that the admixture of these two ingredients results in a tablet having significantly greater adhesion than the natural biopolymer by itself. The adhesion enhancing materials can generally be described as solid polyols having a solubility at room temperature in water greater than about 20 grams of polyol per 100 g of solution (20 g/100 g). Preferably the solubility is greater than about 50 g/100 g, and most preferably the solubility is greater than about 60 g/100 g. In particular, the polyols are sugar alcohols having the above described solubility, and most preferably the sugar alcohols are selected from the group consisting of sorbitol, xylitol and mixtures thereof. The polyol is used in an amount effective to provide a significantly greater adhesion to mucous membranes over that achieved by the natural biopolymer alone. Usually increases of adhesion of at least about 10%, as measured by the force necessary to separate the tablet from a mucous membrane, is considered significant. In most cases increases greater than about 10% may be achieved. Generally, about 20 to about 60% by weight, based on the weight of the tablet, of the polyol is suitable with about 25 to about 55% by weight being preferred and about 30 to about 50% by weight being most preferred, and about 50% by weight being more preferred.

The tablets of this invention may be used in any convenient size or shape for the delivery of the intended active agent. The tablets may be produced by tabletting techniques well known to those skilled in the art using conventional tabletting apparatus. In the production of the tablets it is convenient to use a lubricant in an amount effective to prevent the formed tablet from sticking to the tabletting apparatus. Generally, a lubricant in an amount of less than about 5% by weight of the composition is suitable with about 0.5 to about 3% being preferred and about 1 to about 2% being most preferred. Lubricants which are useful in the formation of tablets are well known in the art. Examples of such lubricants include, but are not limited to, metallic stearates, such as magnesium stearate, calcium stearate, zinc stearate, mixtures thereof, and the like. Preferably the lubricant is calcium stearate. Other lubricants which may prove useful include hydrogenated vegetable oil, partially hydrogenated vegetable oils, animal fats (e.g. triglycerides), polyethylene glycols, polyoxyethylene monostearate, talc, light mineral oils, sodium benzoate, sodium lauryl sulfate, magnesium lauryl sulfate, talc, and mixtures thereof.

Hydrogenated cottonseed oil, solid vegetable oil, hydrogenated soya oil, and mixtures thereof are commonly used oil lubricants in the tabletting art which may prove useful. If oil lubricants are used, they are generally used in amounts of about 0.4% to about 1% by weight, based on the total weight of the tablet.

Thus, for example, the tablets may be produced from a composition formed by blending the natural biopolymer and adhesion promoting material together in a suitable vessel for a sufficient amount of time to thoroughly mix these ingredients. The blending can take place at room temperature (i.e., about 25° C.). Then any artificial sweeteners, vehicles, lubricants, and solid active agents which may be used are added with any other optional solid ingredients and mixed briefly to obtain a relatively uniform blend. To this mixture there is added any liquid active agents, e.g. flavoring. This final mixture is then thoroughly mixed. There is no criticality in the order of mixing the ingredients utilized; however, since the natural biopolymer and the adhesion enhancing material are the predominant ingredients it is preferred that they be thoroughly blended together first. It is also preferred, to insure optimum adsorption of any liquid active agents, that the vehicle used be added to the blend before the addition of the liquid active agent. The resulting mixture is then compressed and compacted on suitable conventional tabletting apparatus.

If desired, other ingredients known in the art may be incorporated, in effective amounts, into the tablets of this invention. Examples of such other ingredients include: stabilizer/preservatives, excipients/disintegration adjusting agents, binders, vehicles, coloring agents, taste controlling agents and odor controlling agents, mixtures thereof, and the like. Examples of these other ingredients may include: parahydroxybenzoic acid alkyl esters, antioxidants, antifungal agents, and the like, as stabilizers/preservatives; magnesium silicate, light silicic acid anhydride, synthetic aluminum silicate, precipitated calcium carbonate, magnesium aluminum metasilicate, calcium hydrogenphosphate, and the like, as excipients/disintegration adjusting agents; starch, dextrin, tragacanth, gelatin, polyvinyl pyrrolidone, polyvinyl alcohol, and the like, as binders; starch, crystalline cellulose, dextrin, anhydrous calcium phosphate, dextrin, lactose, mannitol, sorbitol, and the like, as vehicles; citric acid, fumaric acid, tartaric acid, menthol, citrus perfumes, and the like, as agents for controlling tastes and smell.

When liquid active agents are used, in order to produce a cohesive tablet, it is preferable to use a vehicle to adsorb the liquid agent. In addition to the vehicles mentioned above, the following vehicles are also suitable, colloidal silica particles (e.g., fumed silica), magnesium aluminum silicate, dextrose, magnesium trisilicate, modified maltodextrin (modified maltodextrins are known in the art and have low bulk densities in comparison to conventional maltodextrins; for example, a modified maltodextrin can have a bulk density in the range of about 3.0 to about 8 lbs/ft$^3$ and preferably about 3.0 to about 6.0 lbs/ft$^3$), and mixtures thereof. A preferred vehicle, particularly for active agents which are liquid flavoring agents, is a colloidal silica material comprising colloidal silica particles sintered together in chain-like formations, which is available commercially under the trademark CAB-O-SIL from Cabot Corp. The vehicle is used in amounts effective to adsorb the liquid active agent. For example, CAB-O-SIL used in amounts of at least about 0.6% by weight of the tablet is suitable for the adsorption of about 1 to about 3 wt. % of a flavor oil, such as a peppermint oil. The amounts of other vehicles used may vary in accordance with the nature of the vehicle and/or the nature of the liquid active agent being adsorbed and/or the tabletting conditions (e.g. pressure used to compress the composition and the duration of the compression). The amounts of the vehicle may be therefore varied in accordance with the result desired for the final product and such variations are well within the capabilities of those skilled in the art without the need for undue experimentation. While amounts greater than about 0.1% by wt. may prove useful, in general amounts of at least about 0.6% by wt. of the tablet are suitable.

Effective amounts of active agents are used and the active agents contemplated for use herein are any materials or compounds suitable for oral administration in relatively small amounts over a period of time. Those skilled in the art will appreciate that the amount of active agent which can be delivered depends in part on the size of the final tablet produced. The size of the tablet is generally only limited by what would be considered comfortable for oral use by the consumer. Generally, an acceptable sized tablet weighs about 80 to about 150 mg with about 80 to about 105 mg being preferred, and about 80 to about 100 mg being most preferred. Examples of such active agents include but are not limited to flavoring agents (flavors or flavorings); breath fresheners, such as chlorophyll, metallic salts used as copper gluconate, zinc chloride, and the like, natural vegetable oils, such as cottonseed oil and the like; anti-cariogenic compounds such as the metallic salts of fluorine, e.g., orally ingestible fluorides such as sodium fluoride, sodium monofluorophosphate, stannous fluoride, amine fluorides and the like; local anesthetics such as benzocaine, and the like; oral antiseptics such as chlorhexidine and salts thereof, hexylresorcinol, dequalinium chloride, cetylpyridinium chloride, and the like; anti-inflammatory agents such as triamcinelone, hydrocortisone, and the like; antifungal agents such as miconazole, nystatin, and the like; antiplaque agents such as chlorhexidine and salts thereof, octenidine, and mixtures of thymol, menthol, methysalicylate, and eucalyptol, and the like; tooth densitizers such as potassium nitrate and the like; mixtures thereof; and the like. While the amount of the active agent used may depend upon the type of agent used and the condition being treated, and such amounts are readily determined by those skilled in the art without undue experimentation, the tablets can contain up to about 15% by weight of active agent with up to about 10% being preferred.

In one particular embodiment of this invention the active agent is a flavoring agent (flavors or flavoring). The flavoring agent can either be a solid or liquid, and if a liquid, as discussed above, the liquid will be adsorbed onto a vehicle. The flavoring agent is released over time (sustained release), from the tablets of this invention, without having to encapsulate the flavoring agent. Thus, encapsulation of the flavoring agents are not necessary.

The flavorings that may be used include those known to the skilled artisan, such as, natural and artificial flavors. These flavorings may be chosen from synthetic flavor oils and flavoring aromatics, and/or oils, oleo resins and extracts derived from plants, leaves, flowers, fruits and so forth, and combination thereof. Representative flavor oils include: spearmint oil, cinnamon oil, oil of wintergreen (methylsalicylate), peppermint oils, clove oil, bay oil, anise oil, eucalyptus oil, thyme oil, cedar leaf oil, oil of nutmeg, oil of sage, oil of bitter almonds and cassia oil. Also useful are artificial, natural or synthetic fruit flavors such as vanilla, and citrus oil, including lemon, orange, grape, lime and grapefruit and fruit essences including apple, pear, peach, strawberry, raspberry, cherry, plum, pineapple, apricot and so forth. These flavorings may be used individually or in admixture. Commonly used flavors include mints such as peppermint, menthol, artificial vanilla, cinnamon derivatives, and various fruit flavors, whether employed individually or in admixture.

Flavorings such as aldehydes and esters including cinnamyl acetate, cinnamaldehyde, citral diethylacetal, dihydrocarvyl acetate, eugenyl formate, p-methylamisol, and so forth may also be used. Generally any flavoring or food additive such as those described in *Chemicals Used in Food Processing*, pub 1274 by the National Academy of Sciences, pages 63–258 may be used.

Further examples of aldehyde flavorings include, but are not limited to: acetaldehyde (apple); benzaldehyde (cherry, almond); anisic aldehyde (licorice, anise); cinnamic aldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde butter, cheese); valeraldehyde butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e., trans-2 (berry fruits); tolyl aldehyde (cherry, almond); veratraldehyde (vanilla); 2,6-dimethyl-5-heptenal, i.e., Melonal (melon); 2,6-dimethyloctanal (green fruit); and 2-dodecenal (citrus, mandarin); cherry; grape; strawberry shortcake; mixtures thereof; and the like.

The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. In general, amounts of about 0.5% to about 3.0% by weight of the composition are useable with amounts of about 1% to about 2.5% being preferred and amounts of about 1.5% to about 2% being most preferred.

The tablets of this invention can optionally contain artificial and/or high intensity sweeteners in effective amounts and such amounts are normally a matter of preference. Thus, the amount may be varied in order to obtain the result desired in the final product. Such variations are within the capabilities of those skilled in the art without the need for undue experimentation. In general, the sweeteners are used in amounts of about 0.005% to about 5.0% by weight of the tablet with about 0.05% to about 2.5% being preferred, about 0.1% to about 1% being most preferred, and about 0.1% to about 0.5% being more preferred. Examples of such sweeteners include but are not limited to: the soluble saccharin salts, i.e., sodium or calcium saccharin salts; cyclamate salts; acesulfame-K; the free acid form of saccharin; thaumatin; dihydrochalcones; monellin; steviosides; glycyrrhizin; sucralose; L-aspartic acid derived sweeteners such as L-aspartyl-L-phenylalanine methy ester (APM), L- α-aspartyl-N-(2,2,4,4-tetramethyl-3-thiethanyl)-D-alaninamide hydrate, methyl esters of L-aspartyl-L-phenylglycine and L-aspartyl-2,S,dihydrophenylglycine, L-aspartyl-2,5-dihydro-L-phenylalanine; L-aspartyl-L-(1-cyclohexy-en)alanine, and the like; and the like. Preferably, sodium saccharin is used.

The tablets of this invention may also contain effective amounts of coloring agents. Coloring agents (colorants or colors) which may be used include titanium dioxide and may be used in amounts up to about 2 wt % and preferably up to about 1 wt %. Also, the colorants may include other dyes suitable for food, drug and cosmetic applications, and known as F.D. & C. dyes and lakes. The materials acceptable for the foregoing spectrum of use are preferably water-soluble, and include indigoid dye, known as F.D. & C. Blue No. 2, which is the disodium salt of 5,5-indigotindisulfonic acid. Similarly, the dye known as F.D. & C. Green No. 1 comprises a triphenylmethane dye and is the monosodium salt of 4-[4-N-ethyl-p-sulfobenzylamino)diphenylmethylene]-[1-N-ethyl-N-p-sulfoniumbenzyl)- $\Delta^{2,5}$-cyclothylene hexadienimine]. A full recitation of all F.D. & C. and D. & C. dyes and their corresponding chemical structures may be found in the Kirk-Othmer Encyclopedia of Chemical Technology, at Volume 5, Pages 857–884, which text is accordingly incorporated herein by reference.

Those skilled in the art will appreciate that the total amount of all ingredients (components) used in the tablets of this invention equals 100% by weight of the total tablet. Also, unless stated otherwise, all percents herein are percent by weight of the total tablet.

The following examples are illustrative only and should not be construed as limiting the invention in any way. Those skilled in the art will appreciate that variations are possible which are within the spirit and scope of the appended claims.

In the examples that follow, the xanthan gum used was Keltrol TF obtained from Kelco, Division of Merck & Co., Inc.

EXAMPLE 1

Tablets, about 100 mg each, of this invention were prepared from about a 5000 mg batch having the formulation given in Table I.

TABLE I

| Ingredient | Amount (mg) | % by Wt. |
|---|---|---|
| Xanthan gum | 3400 | 66 |
| Sorbitol | 1500 | 30 |
| Peppermint oil | 100 | 2 |
| Sodium saccharin | 15 | 0.3 |
| Calcium stearate | 50 | 1 |
| CAB-O-SIL | 30 | 0.6 |

The tablets were prepared by blending the xanthan gum and sorbitol together, using a mortar and pestle, at room temperature (about 25° C.) for about 5 to about 7 minutes until thoroughly mixed.

The sodium saccharin, CAB-O-SIL and calcium stearate were then added to the xanthan gum/sorbitol mixture. These components were then briefly mixed together for about 1 to about 2 minutes. Then the peppermint oil was added and the components were mixed thoroughly.

Tablets were made by placing about 100 mg of the above mixture in a Carver Press and compressing for about 15 seconds under a pressure of about 5000–6000 psi;

The tablets were found to have good adhesiveness in the mouth with a low, but acceptable, peppermint flavor over a time period of about 2–3 hours.

EXAMPLE 2

Tablets, about 100 mg each, of this invention with sodium fluoride were prepared in accordance with the procedure of Example 1 except that the 5000 mg batch had the formulation set forth in Table II.

TABLE II

| Ingredient | % by Wt. |
| --- | --- |
| Xanthan gum | 66 |
| Sorbitol | 30 |
| Peppermint oil | 2 |
| Sodium saccharin | 0.3 |
| Calcium stearate | 1 |
| CAB-O-SIL | 0.6 |

The sodium fluoride composition was prepared by taking 90% by weight of the formulation in Table II and blending it with 10% by weight of sodium fluoride. Thus, each about 100 mg tablet contained about 90 mg of the Table II formulation and about 10 mg sodium fluoride.

EXAMPLE 3

A dissolution study, to determine % release of fluoride versus time, was made of the sodium fluoride containing tablets from Example 2. The study was conducted by taking one tablet and placing it in 100 ml of deionized water at 37° C., one ml aliquots were taken at appropriate time intervals with the aliquot taken being replaced by deionized water to maintain 100 ml of solution. The fluoride ion content of the aliquot as well as maximum fluoride ion content was assayed using a specific fluoride ion electrode. The results are given in Table III.

TABLE III

| Time (min.) | Fluoride Ion in Aliquot (mmolar) | % Release |
| --- | --- | --- |
| 0 | 0.0065 | 0.3 |
| 10 | 0.486 | 20.4 |
| 20 | 0.797 | 33.5 |
| 40 | 1.22 | 51.3 |
| 60 | 1.56 | 65.5 |
| 90 | 1.80 | 75.6 |
| 120 | 2.08 | 87.4 |
| 150 | 2.16 | 90.8 |
| 180 | 2.16 | 90.8 |

Maximum fluoride ion: 2.38 mmolar

The results in Table III demonstrate the sustained release of sodium fluoride from tablets of this invention.

EXAMPLE 4

Tablets, about 100 mg each, of this invention were prepared from a 5000 mg batch having the formulation set forth in Table IV. The procedure of Example 1 was followed and the tablets were made using a Carver Press at 6000 psi for 15 seconds.

TABLE IV

| Ingredient | % by Wt. A | B | C |
| --- | --- | --- | --- |
| Xanthan gum | 66 | 46 | 26 |
| Sorbitol | 30 | 50 | 70 |
| Peppermint oil | 2 | 2 | 2 |
| Sodium saccharin | 0.3 | 0.3 | 0.3 |
| Calcium stearate | 1 | 1 | 1 |
| CAB-O-SIL | 0.6 | 0.6 | 0.6 |

When a tablet of each of Runs A-C were placed on the roof of the mouth the results set forth in Table V were observed

TABLE V

| Run | Time of adhesion/sustained release of peppermint oil and sweetness |
| --- | --- |
| A | about 1¾ hrs. |
| B | about 60 minutes |
| C | about 30 minutes |

EXAMPLE 5

Tablets, 100 mg each, of this invention were prepared using the procedure of Example 1. The tablets comprised about 30%, 50% and 70% by wt. sorbitol according to the formulations given in Table IV, Runs A, B and C, respectively. Tablets were prepared having no (0%) sorbitol but having the following formulation: 96% by wt. xanthan gum, 2% by wt. peppermint oil, 0.3% sodium saccharin, 1% calcium stearate and 0.6% CAB-O-SIL.

The tablets were tested for their bioadhesion using a procedure disclosed in U.S. Pat. No. 4,615,697 issued to Robinson on Oct. 7, 1986, the disclosure of which is incorporated herein by reference thereto. Some modifications were made in the procedure disclosed by Robinson.

Those modifications were as follows: artificial saliva was used instead of gastric fluid; the artificial saliva was adjusted to the level of the tissue, the tissue was not immersed, i.e., just enough artificial saliva was used to wet the tissue; the tissue used was frozen rabbit stomach which was thawed in about a 0.8% by wt. sodium chloride solution at about 5° C. for about 1 hour; 10 microliters of artificial saliva was added to the area on the tissue where the tablet was to be lowered into contact with the tissue, the tablet was glued to a No. 0 rubber stopper; the combined weight of the stopper and the tablet was the force used to adhere the tablet to the tissue by allowing the stopper and tablet to rest on the tissue for one minute; the temperature of the artificial saliva was maintained at about 37° C. using a water bath; and a modified Roller-Smith Scale was used to determine the force, in mg, necessary to separate the tablet from the tissue, the scale was modified by making about a 1 inch hole in the platform of the balance to accommodate the wire which was attached to the rubber stopper.

The artificial saliva utilized was prepared from the following components: 2 g KCNS, 14 g KCl, 1.8 g $NaH_2PO_4$, and 2.0 g $Na_2HPO_4$ dissolved in enough water to make a 1 liter solution. This solution was then diluted by a factor of 10 and the diluted solution was utilized in the procedure for the adhesion measurement.

The results obtained are reported in Table VI and graphically represented in FIG. 1. In Table VI, the Total Net Force To Separate refers to the net force needed to separate the stopper with the tablet from the tissue.

TABLE VI

| % by wt. Sorbitol | Test Run | Total Net Force To Separate (mg) | Average of Test Runs |
| --- | --- | --- | --- |
| 0 | 1 | 9734.0 | — |
| 0 | 2 | 9473.8 | — |
| 0 | 3 | 9982.0 | 9729.9 |
| 30 | 1 | 10896.8 | — |
| 30 | 2 | 11210.2 | — |

TABLE VI-continued

| % by wt. Sorbitol | Test Run | Total Net Force To Separate (mg) | Average of Test Runs |
|---|---|---|---|
| 30 | 3 | 9996.0 | — |
| 30 | 4 | 11164.0 | 10816.8 |
| 50 | 1 | 15395.1 | — |
| 50 | 2 | 12715.6 | — |
| 50 | 3 | 14275.6 | 14128.8 |

EXAMPLE 6

Following the procedure of Example 5, about 100 mg tablets were made up having about 0%, 30%, 50%, 70% and 90% by wt. sorbitol, about 50% by wt. xylitol, and about 50% by wt. mannitol. The tablets were tested for their degree of adhesion in accordance with the procedure of Example 5.

The tablets containing about 90% by wt. sorbitol had the following formulation: 6% by wt. of xanthan gum, 90% by wt. sorbitol, 2% by wt. peppermint oil, 0.3% by wt. sodium saccharin, 1% by wt. calcium stearate, and 0.6% by wt. CAB-O-SIL.

The tablets containing about 50% by wt. xylitol or mannitol had the following formulation: 46% by wt. xanthan gum, 50% by wt. xylitol or mannitol, 2% by wt. peppermint oil, 0.3% by wt. sodium saccharin, 1% by wt. calcium stearate, and 0.6% by wt. CAB-O-SIL.

Figure 2:
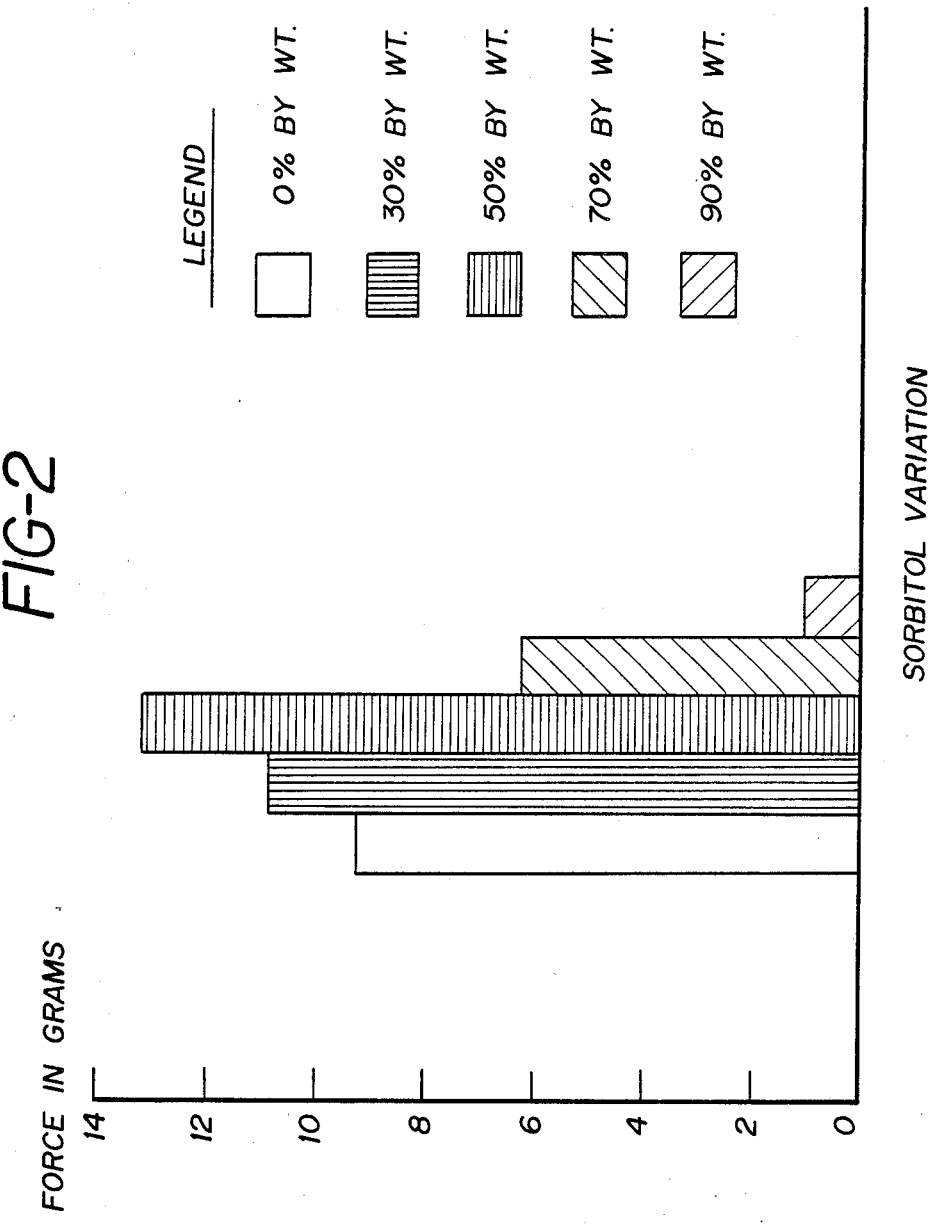
FIG. 2 is a bar graph illustrating the effect on bioadhesion of different concentrations of sorbitol in xanthan gum tablets.
Figure 3:
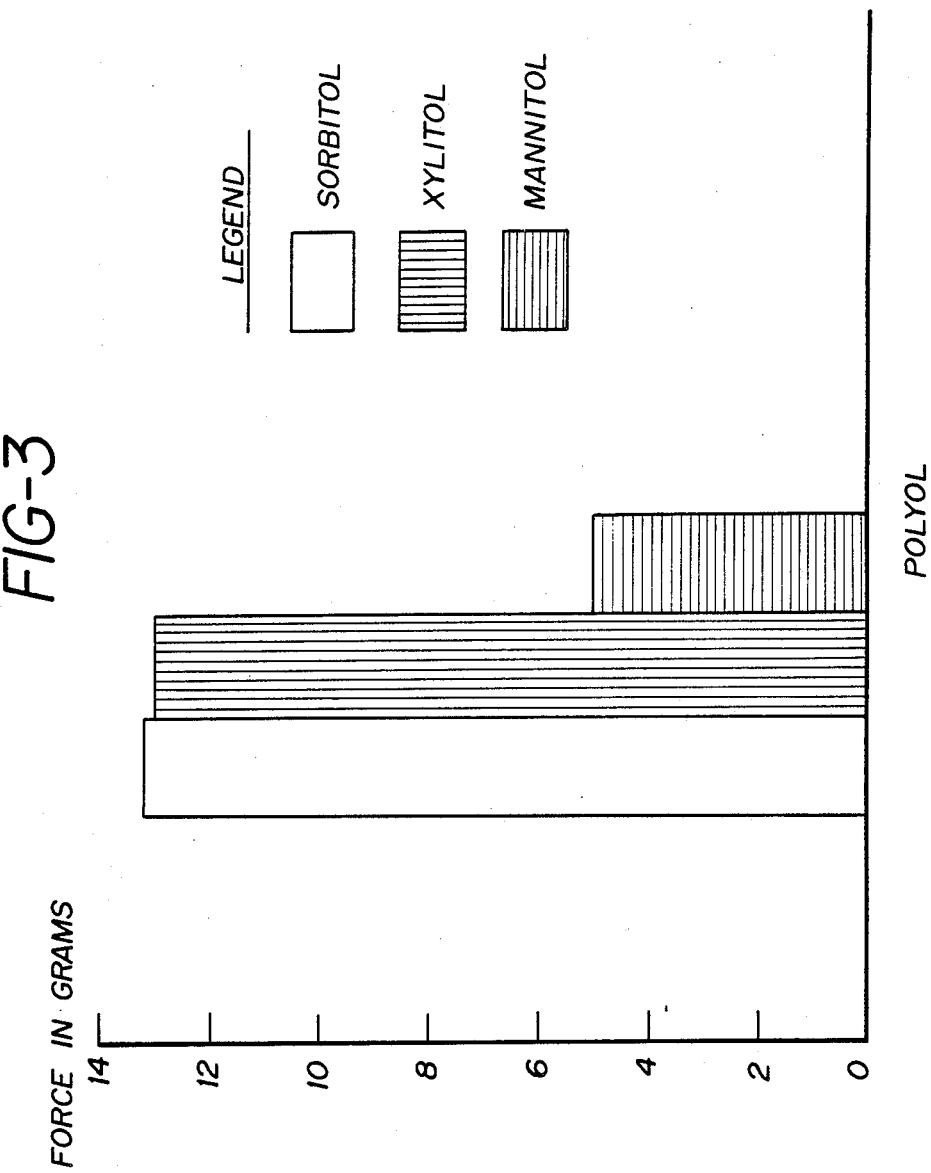
FIG. 3 is a bar graph illustrating the effect on bioadhesion of 50% by wt. sorbitol, xylitol, and mannitol in xanthan gum tablets.

The results obtained for the adhesion measurements are reported in Table VII for sorbitol, Table VIII for xylitol, and Table IX for mannitol. The results in Table VII are graphically illustrated in FIG. 2, and the results in Tables VIII and IX are graphically illustrated in FIG. 3. In FIG. 3 the bar for 50% by wt. sorbitol represents the same results reported in Table VII and illustrated in FIG. 2. In Tables VII-IX, the Total Net Force To Separate refers to the net force needed to separate the stopper with the tablet from the tissue.

TABLE VII

| % by wt. Sorbitol | Test Run | Total Net Force To Separate (mg) | Average of Test Runs |
|---|---|---|---|
| 0 | 1 | 9398.2 | — |
| 0 | 2 | 9137.4 | — |
| 0 | 3 | 9225.0 | 9253.5 |
| 30 | 1 | 10532.8 | — |
| 30 | 2 | 11261.6 | 10897.2 |
| 50 | 1 | 12603.4 | — |
| 50 | 2 | 13793.8 | 13198.6 |
| 70 | 1 | 6062.4 | — |
| 70 | 2 | 6420.0 | 6241.2 |
| 90 | 1 | 1100.2 | — |
| 90 | 2 | 978.4 | 1039.3 |

TABLE VIII

| % by wt. Xylitol | Test Run | Total Net Force To Separate (mg) | Average of Test Runs |
|---|---|---|---|
| 50 | 1 | 12758.2 | — |
| 50 | 2 | 13243.8 | 13001.0 |

TABLE IX

| % by wt. Mannitol | Test Run | Total Net Force To Separate (mg) | Average of Test Runs |
|---|---|---|---|
| 50 | 1 | 6049.2 | — |
| 50 | 2 | 5826.8 | — |
| 50 | 3 | 4005.4 | — |
| 50 | 4 | 4047.6 | 4982.3 |

The results obtained in Example 6 demonstrate that there is a range for the amount of sugar alcohol used within which the sugar alcohols operate to increase bioadhesion. Increasing the amount of sugar alcohol above the upper limit of this range decreases bioadhesion. It is surprising that since the xanthan gum is the bioadhesive material that replacing as much as about 50% by wt. of the xanthan gum with a sugar alcohol of this invention continues to significantly increase bioadhesion. This is surprising because one skilled in the art might expect that reducing the amount of bioadhesive material in this manner might result in a concomitant reduction in bioadhesion and not an increase.

These results also demonstrate that the tablets containing 30% and 50% by wt. sorbitol and 50% by wt. xylitol represent tablets of this invention; however, the tablets containing 90% by wt. sorbitol and 50% by wt. mannitol do not represent tablets of this invention. Without wishing to be bound by theory, these results may be related to the solubilities of the various sugar alcohols. Mannitol has a solubility of about 18 g mannitol per 100 g of solution (18 g/100 g), whereas sorbitol has a solubility of about 83 g sorbitol per 100 g of solution (83 g/100 g) and xylitol has a solubility of about 64 g xylitol per 100 g of solution (64 g/100 g), the solubilities given being maximum solubility in water at room temperature. Thus, mannitol is much less soluble than either sorbitol or xylitol.

The invention being thus described, it will be obvious that the same may be varied in many ways. Such variations are not to be regarded as a departure from the spirit and scope of the invention and all such modifications are intended to be included within the scope of the claims.

What is claimed is:

1. A tablet having improved bioadhesion to mucous membranes comprising:
    (a) a water-soluble natural biopolymer in an amount of from about 40 to about 80 weight percent of the tablet, selected from the group consisting of a xanthan gum, a pectin and mixtures thereof; and
    (b) a solid polyol in an amount of from about 20 to about 60 weight percent of the tablet and having a solubility at room temperature in water greater than about 20 grams of polyol per 100 g of solution.

2. A tablet having improved bioadhesion to mucous membranes comprising
    (a) a xanthan gum present in amounts of about 40 to about 80% by weight of the composition;
    (b) a sugar alcohol having a solubility at room temperature in water greater than about 20 g per 100 g solution selected from the group consisting of sorbitol, xylitol, and mixtures, said sugar alcohol being present in an amount of about 20 to about 60% by weight of the composition; wherein there is additionally included an effective amount of a lubricant; wherein there is additionally included an effective amount of an active ingredient selected from the group consisting of flavorings, local anesthetics, local antiseptics, anti-cariogenic compounds, anti-inflammatory agents, antifungal agents, antiplaque agents, tooth desensitizers and mixtures thereof; wherein there is optionally included an effective amount of a vehicle; and wherein there is included an effective amount of sweetener selected from the group consisting of artificial sweeteners, high intensity sweeteners, and mixtures; such that the total of all components equals 100%.

3. The tablet of claim 2 wherein said active ingredient is a liquid flavoring and said vehicle is present.

4. The tablet of claim 1 wherein said biopolymer is present in amounts of about 50 to about 70% by weight of the composition and said polyol is present in amounts of about 30 to about 50% by weight of the composition.

5. The tablet of claim 1 wherein said polyol is a sugar alcohol.

6. The tablet of claim 1 wherein said polyol is a sugar alcohol selected from the group consisting of sorbitol, xylitol, and mixtures thereof.

7. The tablet of claim 6 wherein said sugar alcohol is present in an amount of about 20 to about 60% by weight of the tablet and the biopolymer is present in an amount of about 40 to about 80% by weight of the tablet.

8. The tablet of claim 7 wherein said sugar alcohol is present in an amount of about 30 to about 50% by weight and said biopolymer is present in an amount of about 50 to about 70% by weight.

9. The tablet of claim 2 wherein said biopolymer is a xanthan gum.

10. The tablet of claim 7 wherein said biopolymer is a xanthan gum.

11. The tablet of claim 8 wherein said biopolymer is a xanthan gum.

12. The tablet of claim 1 wherein there is additionally included an effective amount of a lubricant.

13. The tablet of claim 12 wherein said lubricant is selected from the group consisting of metallic stearates and mixtures thereof.

14. The tablet of claim 13 wherein said lubricant is calcium stearate.

15. The tablet of claim 1 wherein there is additionally included effective amounts of an active agent selected from the group consisting of: flavorings, local antiseptics, local anesthetics, anti-cariogenic compounds, anti-inflammatory agents, antifungal agents, antiplaque agents, tooth desensitizers, and mixtures thereof.

16. The tablet of claim 15 wherein said active agent is a liquid and said tablet additionally contains an effective amount of a vehicle.

17. The tablet of claim 16 wherein said vehicle is selected from the group consisting of colloidal silica particles, magnesium aluminum silicate, dextrose, magnesium trisilicate, modified maltodextrin, and mixtures thereof.

18. The tablet of claim 17 wherein the active agent is a flavoring.

19. The tablet of claim 18 wherein said flavoring is selected from the group consisting of spearmint oil, cinnamon oil, oil of wintergreen, peppermint oil, and mixtures thereof.

20. The tablet of claim 17 wherein said vehicle is comprised of colloidal silica particles sintered together in chain-like formations.

21. The tablet of claim 1 wherein there is additionally included an effective amount of a sweetener selected from the group consisting of artificial sweeteners, high intensity sweeteners, and mixtures thereof.

22. The tablet of claim 15 wherein said active agent is an anti-cariogenic material comprising an orally ingestible fluoride containing compound.

23. The tablet of claim 22 wherein said active ingredient is selected from the group consisting of sodium fluoride, sodium monofluorophosphate, stannous fluoride and mixtures thereof.

24. The tablet of claim 2 wherein said xanthan gum is present in an amount of about 50 to about 70% by weight of the composition and said sugar alcohol is present in an amount of about 30 to about 50% by weight of the composition.

* * * * *